United States Patent [19]
Olbrich et al.

[11] Patent Number: 5,760,221
[45] Date of Patent: Jun. 2, 1998

[54] METHOD FOR THE PREPARATION OF HEXAHYDROAZEPINONES AND HEXAHYDROAZEPINOLES

[75] Inventors: Alfred Olbrich, Obertshausen; Jürgen Engel, Alzenau; Bernhard Kutscher, Maintal; Roland Möller, Hammersbach, all of Germany

[73] Assignee: ASTA Medica Aktiengesellschaft, Dresden, Germany

[21] Appl. No.: 359,457

[22] Filed: Dec. 19, 1994

[30] Foreign Application Priority Data

Dec. 18, 1993 [DE] Germany .................. 43 43 409.6

[51] Int. Cl.$^6$ .............. C07D 267/02; C07D 281/02; C07D 243/00; C07D 223/08
[52] U.S. Cl. .............. 540/544; 540/553; 540/604
[58] Field of Search .............. 540/544, 553, 540/604

[56] References Cited

U.S. PATENT DOCUMENTS 3,813,384  5/1974  Vogelsang et al. .............. 260/239

FOREIGN PATENT DOCUMENTS

| 2206385 | 8/1973 | Germany .............. C07D 498/04 |
| 3530793 | 3/1986 | Germany .............. C07D 403/04 |
| 3634942 A1 | 5/1987 | Germany . |
| 1412377 | 11/1975 | United Kingdom .............. 498/4 |

OTHER PUBLICATIONS

Scheffler et al., "Synthese und Kristallstrukturanalyse von Azelastin", *Arch. Pharm.* (Weinheim), vol. 321, 1988, pp. 205–208.
John Wiley & Sons, Inc., Organic Reactions, vol. 15, 1967, pp. 1–13, p. 40.
Published by the Chemical Society of Japan, vol. 31, No. 4, May 1958, pp. 418–422.
Collection of Czechoslovak Chemical Communications, vol. 51, 1986, pp. 2034–2049.

*Primary Examiner*—Mukund J. Shah
*Assistant Examiner*—Brenda Coleman
*Attorney, Agent, or Firm*—Cushman Darby & Cushman IP Group of Pillsbury Madison & Sutro LLP

[57] ABSTRACT

This disclosure describes two technical procedures for the high-yield synthesis of heterocyclic seven-membered ring-systems by Dieckmann-condensation avoiding usual dilution techniques and long reaction times. Thus, it significantly increases the overall yields of the pharmaceutically active ingredients azelastine and flezelastine, whose synthesis, starting from these seven-membered heterocyclic rings, is reported elsewhere. Yields range from 80–89%, avoiding waste and increasing economics of the synthesis.

8 Claims, 1 Drawing Sheet

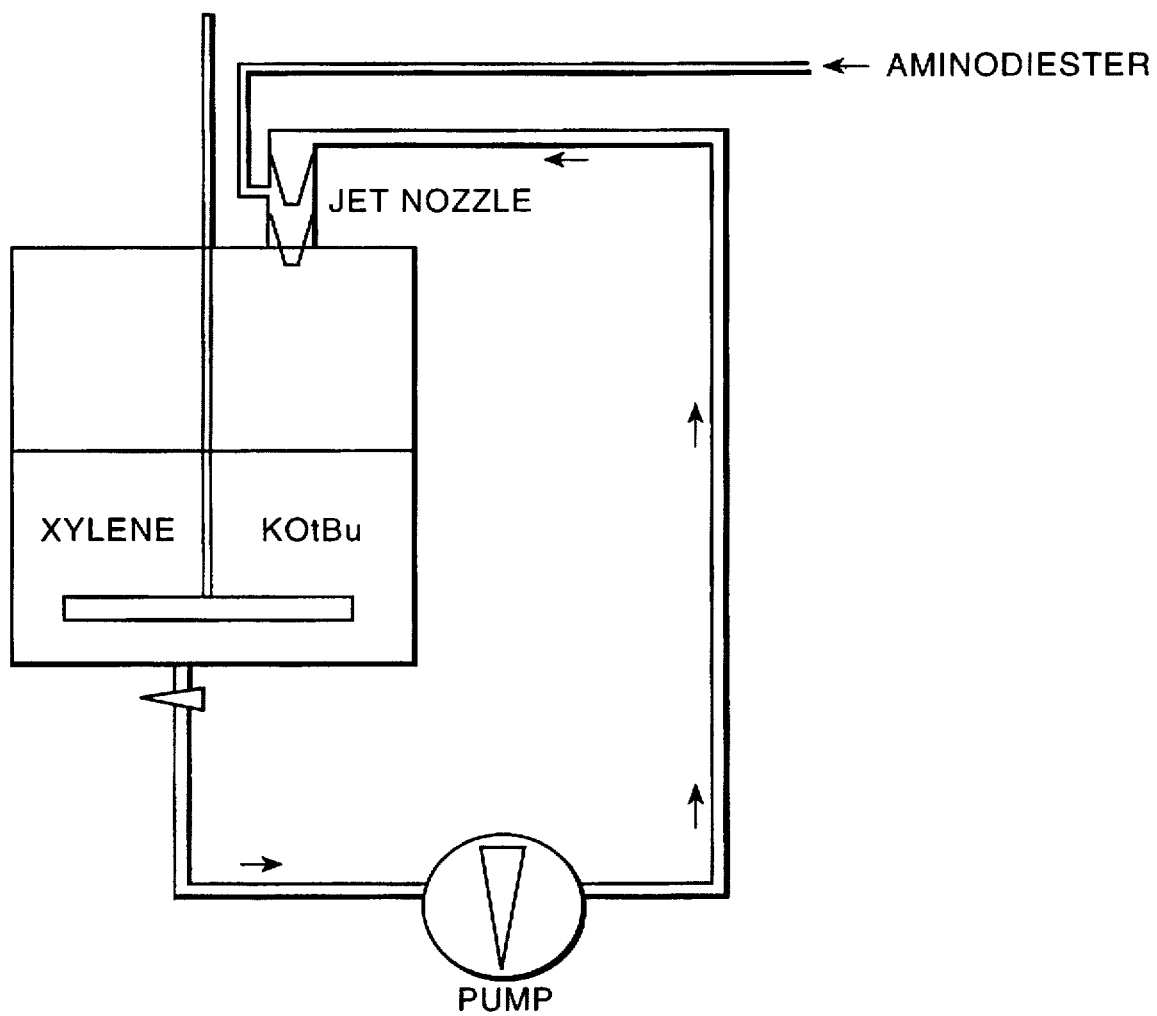

METHOD FOR THE PREPARATION OF HEXAHYDROAZEPINONES AND HEXAHYDROAZEPINOLES

The present invention relates to an improved method for the preparation of hexahydroazepinones and hexahydroazepinoles of the general formula I

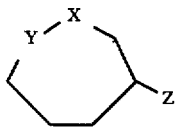

wherein

X signifies —N(—), —CH$_2$—, —S—, —O—

Y signifies N(—R)—, —N(—CH$_3$), or signifies N(—CH$_2$—CH$_2$—C$_6$H$_5$) and

Z signifies O, —OH, wherein in each case R represents H, alkyl, cycloalkyl, aralkyl, aryl and the addition salts thereof.

Heterocyclic ketones having seven-membered rings are important intermediate products for the synthesis of pharmacologically active substances. These include structures of the azelastine type (INN) and the flezelastine type (INN), which have antiasthmatic and antiallergic properties (for example, DE-OS 3634942/Drugs Of The Future 12 (3), 283 (1987/EP 488209), as well as structures for the treatment of disorders of the central nervous system such as Parkinsonism, hyperprolactinaemia and schizophrenia or for the treatment of cardiovascular diseases (for example, DE-OS 3820775).

Fungicidally active substances containing a heterocyclic seven-membered ring are also known.

Moreover, derivatives of the phospholipid type containing a heterocyclic seven-membered ring have antineoplastic activity.

PRIOR ART

A comprehensive survey of the Dieckmann condensation is found in Org. Reactions, Vol. 15, 1–203 (1967) and in the references cited there.

Three criteria are invariably emphasised in the synthesis of seven-membered and higher-membered rings:

1. high dilution in order to promote the intramolecular as against the intermolecular reaction
2. long reaction times (slow dropwise addition of the 1.8 acid ester in order to promote the 1,8 intramolecular reaction)
3. large excesses of the base employed.

The greatly varying yields are also noticeable, even in the preparation of identical products by different working groups.

Alternative methods of preparation such as

Friedel-Crafts acylation (J. Chem. Soc., Perkin Trans. I 1992, 445)

ring enlargement using diazomethane (Bull. Chem. Soc., Japan, 31, 418 (1958) ; Coll. Czech. Chem. Commun., 51, 2034 (1986))

ozonolysis of cyclohexenone followed by a reductive amino cyclisation (Synth. Commun., 21 (7), 881 (1991) do not lead to satisfactory yields of the desired products, quite apart from the technical achievement of ozonolysis or the handling of diazomethane.

The object of the invention is to develop a method for the large-scale preparation of heterocyclic ketones having seven-membered rings, based on the well-known Dieckmann condensation reaction.

The invention relates to the preparation of salts of heterocyclic ketones having seven-membered rings by means of Dieckmann condensation.

The operation is such 8-dicarboxylic acid ester of the formula II

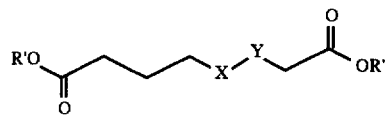

wherein X signifies —CH$_2$—, Y signifies —N(—R)—, —N(—CH$_3$)— or signifies —N(—CH$_2$—CH$_2$—C$_6$H$_5$)—, and R' is an alkyl, isoalkyl, cycloalkyl, aralkyl, aryl group, obtainable by known methods is reacted with strong bases in an inert solvent. Following acid hydrolysis of the cyclic β-enolate carboxylic acid ester formed, the ester is saponified without being isolated and thermally decarboxylated. The resulting heterocyclic ketone having a seven-membered ring is subsequently separated from the reaction mixture in the form of its acid addition salt and isolated in pure form.

Surprisingly, it was found that the parameters of long reaction time, large excess of bases and high dilution do not (as hitherto assumed) influence the amount of the yield in a particular way. At reaction times of from 1 to 6 hours, preferably 1 to 3 hours, and excesses of base of from 0% to a maximum of 20%, it was possible to establish technical conditions for carrying out the dilution without resorting to large quantities of solvent and hence greatly increase the production output.

To this end two methods were developed.

1. The base, which is dissolved in an inert solvent, is circulated. A jet nozzle is positioned in the circulation loop, similar to the principle of the water-jet pump. The 1,8 dicarboxylic acid ester is introduced undiluted into the side inlet of the nozzle (see FIG. 1).

2. The ascending vapour along a packed column is used to dilute the undiluted 1,8 dicarboxylic ester, which is charged at the top of the column. A practical side-effect is that the diester is thereby brought to the reaction temperature and, by means of a suitable solvent, can also be dissolved in the column and freed from volatile by-products, such as residual solvents. The concentrations in the two methods described above range between 0.1 and 1.5 mol/l, preferably between 0.3 and 0.9 mol/l (1,8-dicarboxylic ester to solvent initially employed). At the same time as the dicarboxylic ester is added, an azeotropic solvent mixture is separated off at the top of the column, and corresponds in fact to as much as 1 to 3 times the quantitative volume of the 1,8-dicarboxylic acid ester introduced.

Suitable solvents are:

aliphatic ethers such as, for example
   diethyl ether
   tetrahydrofuran
   dioxane
aromatic hydrocarbons such as, for example
   benzene
   toluene
   o-xylene
   m-xylene
   p-xylene
   xylene (isomeric mixture)
   mesitylene The bases which can be employed are:

alkali and alkaline-earth hydrides alkali and alkaline-earth amides alkali and alkaline-earth alcoholates The alcoholcomponents for the 1.8 dicarboxylic acid esters which can be used are:

alkyl alcohols isoalkyl alcohols cycloalkyl alcohols as well as aralkyl alcohols or aryl alcohols.

The present invention is illustrated in more detail by the following examples.

Example 1

A side stream of 245.3 g of ethyl 4-(2-carbethoxyethyl-methylamino)butyrate is charged evenly under nitrogen over a period of 2 hours into a solution of 123.4 g of potassium tert-butylate in 1.3 l of boiling xylene pumped round a loop reactor and the mixture is allowed to react for a further 0.5 hours. 750 ml of azeotrope is distilled off. The reaction mixture is hydrolysed at 50° to 80° C. by rapid addition to a mixture of 300 ml of concentrated (37%) hydrochloric acid and 500 g of crushed ice. The organic layer separated off is washed twice, each time with 150 ml of semi-concentrated hydrochloric acid. The combined aqueous extracts are heated for 2 hours under vigorous reflux and then evaporated to dryness in vacuo. The residue is dissolved in 700 ml of isopropanol, filtered off hot from the undissolved potassium chloride and crystallised at 0° to −5° C. The residue filtered off is dried to constant weight in vacuo at elevated temperature. A second fraction can be obtained by concentrating the mother liquor to a volume of approximately 100 ml. 141.6 g (86.6%) of 1-methyl-perhydroazepin-4-one HCl is obtained.

Melting point: 167° C. (decomposition)

Example 2

A side stream of 245.3 g of ethyl 4-(2-carbethoxyethyl-methylamino)butyrate dissolved in 900 ml of xylene is charged evenly under nitrogen over a period of 3 hours into a solution of 123.4 g of potassium tert-butylate in 1.3 l of boiling xylene pumped around a loop reactor and the mixture is allowed to react for a further 1.5 hours. 1500 ml of azeotrope is distilled off. The reaction mixture is hydrolysed at 50° to 80° C. by rapid addition to a mixture of 300 ml of concentrated (37%) hydrochloric acid and 500 g of crushed ice. The organic layer separated off is washed twice, each time with 150 ml of semi-concentrated hydrochloric acid. The combined aqueous extracts are heated for 2 hours under vigorous reflux and then evaporated to dryness in vacuo. The residue is dissolved in 700 ml of isopropanol, filtered off hot from the undissolved potassium chloride and crystallised at 0° to −5° C. The residue filtered off is dried to constant weight in vacuo at elevated temperature. A second crop of material can be obtained by concentrating the mother liquor to a volume of approximately 100 ml. 145.9 g (89.2%) of 1-methylperhydroazepin-4-one HCl is obtained.

Melting point: 163°–164° C. (decomposition)

Example 3

A side stream of 100 g of ethyl 4-(2-carbethoxyethyl-benzylamino)butyrate is charged evenly under nitrogen over a period of 3 hours into a solution of 43.6 g of potassium tert-butylate in 1.65 l of boiling xylene pumped round a loop reactor and the mixture is allowed to react for a further 1.5 hours. 800 ml of azeotrope is distilled off. The reaction mixture is hydrolysed at 50° to 80° C. by rapid addition to a mixture of 200 ml of concentrated (37%) hydrochloric acid and 500 g of crushed ice. The organic layer separated off is washed twice, each time with 100 ml of semi-concentrated hydrochloric acid. The combined aqueous extracts are heated for 2 hours under vigorous reflux and then evaporated to dryness in vacuo. The residue is exhaustively extracted from isopropanol and crystallised.

The residue filtered off is dried to constant weight in vacuo at elevated temperature. A second crop of materials can be obtained by concentrating the mother liquor to a volume of approximately 100 ml. 60.3 g (80.8%) of 1-benzylperhydro-azepin-4-one HCl is obtained.

Melting point: 191° to 193° C. (decomposition)

Example 4

90.0 kg of ethyl 4-(2-carbethoxyethylmethylamino)butyrate is charged evenly under nitrogen over a period of 2 to 3 hours at the top of the column into a solution of 50.0 kg of potassium tert-butylate in 400 ml of boiling xylene and the mixture is allowed to react for a further 1 to 1.5 hours. Approximately 160 l of azeotrope is distilled off. The reaction mixture is hydrolysed at 50° to 80° C. by rapid addition to a mixture of 80 l of concentrated (37%) hydrochloric acid and 100 g of crushed ice. The organic phase separated off is washed twice, each time with 50 l of semi-concentrated hydrochloric acid. The combined aqueous extracts are heated for 2 hours under vigorous reflux and then evaporated to dryness in vacuo. The residue is dissolved in 400 l of isopropanol, filtered off hot from the undissolved potassium chloride and crystallised at 0° to −5° C. The residue filtered off is dried to constant weight in vacuo at elevated temperature. 43.2 kg (72.0%) of 1-methylperhydroazepin-4-one HCl is obtained.

Melting point: 162°–165° C. (decomposition)

Example 5

168.8 g of ethyl 4-(2-carbethoxyethyl(2-phenyl-ethyl)amino)butyrate (content: 94%) is charged evenly, under nitrogen, over a period of 2 to 3 hours at the top of a packed column into a solution of 61.7 g of potassium tert-butylate in 1.5 l of boiling xylene and the mixture is allowed to react for a further 1 to 1.5 hours. Approximately 500 ml of azeotrope is distilled off. The reaction mixture is hydrolysed at 50° to 80° C. by rapid addition to a mixture of 200 ml of concentrated (37%) hydrochloric acid and 300 g of crushed ice. The organic layer separated off is washed twice, each time with 100 ml of semi-concentrated hydrochloric acid. The combined aqueous extracts are heated for 2 hours under vigorous reflux and then evaporated to dryness in vacuo. The residue is suspended hot in 250 ml of isopropanol and crystallised in the cold. The crystallisate is exhaustively extracted from isopropanol and crystallised. The residue filtered off is dried to constant weight in vacuo at elevated temperature. A second crop of material can be obtained by concentrating the mother liquor to a volume of approximately 100 ml. 107.7 g (89.7%) of 1-(2-phenylethyl)perhydroazepin-4-one HCl is obtained.

Melting point: 196°–198° C. (decomposition)

Example 6

84.5 kg of ethyl 4-(2-carbethoxyethyl(2-phenyl-ethyl)amino)butyrate (content: 92.2%) is charged evenly under nitrogen, over a period of 2 to 3 hours at the top of a packed column into a solution of 30.0 kg of potassium tert-butylate in 400 l of boiling xylene and the mixture is allowed to react for a further 1 to 1.5 hours. Approximately 150 of azeotrope is distilled off. The reaction mixture is hydrolysed at 50° to 80° C. by rapid addition to a mixture of 60 l of concentrated (37%) hydrochloric acid and 60 g of crushed ice. The organic phase separated off is washed twice, each time with 30 of of semi-concentrated hydrochloric acid. The combined aqueous extracts are heated for 2 hours under vigorous reflux and then evaporated to dryness in vacuo. The residue is exhaustively extracted from isopropanol and crystallised. The residue filtered off is dried to constant weight in vacuo at elevated temperature. 40.0 kg (67.8%) of 1-(2-phenylethyl)perhydroazepin-4-one HCl is obtained.

Melting point: 196°–198° C. (decomposition)

Elemental analysis: calculated: C 66.26 H 7.95 N 5.52 found: C 66.24 H 7.94 N 5.43

Assay (Cl⁻): 100.28%

Example 7

100 ml of 1N sodium hydroxide solution is added to a solution of 18.9 g of sodium borohydride in 100 ml of water. A solution of 163.6 g of 1-methylperhydroazepin-4-one HCl in 100 ml of water is added dropwise at an internal temperature of 0° to 5° C. The mixture is stirred for 2 hours at 0° to 5° C. and then for 2 hours at room temperature. The pH is adjusted to 2 to 3 by addition of semi-concentrated hydrochloric acid. The mixture is evaporated to dryness in vacuo, the residue is taken up in 600 ml of isopropanol, the inorganic salts are separated off at 60° to 75° C. and the product is crystallised in an ice bath. The product is filtered and dried to constant weight in vacuo at elevated temperature. 149 g (90%) of 1-methylperhydroazepin-4-ol HCl is obtained.

Melting point: 156°–158° C.

Example 8

34.0 kg of ethyl 4-(2-carbethoxyethylmethylamino) butyrate dissolved in 400 l of xylene is charged evenly under nitrogen over a period of 2 to 3 hours into a suspension of 5.0 kg of sodium hydride (80% in mineral oil) in 200 l of boiling xylene and allowed to react for a further 0.5 hours. Approximately 400 l of azeotrope is distilled off. The reaction mixture is hydrolysed at 50° to 80° C. by rapid addition to a mixture of 35 l of concentrated (37%) hydrochloric acid and 60 g of crushed ice. The organic layer separated off is washed twice, each time with 30 l of semi-concentrated hydrochloric acid. The combined aqueous extracts are heated for 2 hours under vigorous reflux and then evaporated to dryness in vacuo. The residue is dissolved in 100 l of isopropanol, filtered off hot from the undissolved potassium chloride and crystallised at 0° to –5° C. The residue filtered off is dried to constant weight in vacuo at elevated temperature. 11.7 kg (52.0%) of 1-methyl-perhydroazepin-4-one HCl is obtained.

Melting point: 162°–164° C.

Example 9

245.3 g of ethyl 4-(2-carbethoxyethylmethylamino) butyrate is charged evenly, under nitrogen, over a period of 1.75 hours into a solution of 39.0 g of sodium hydride (80% in white mineral oil) and 75 ml of ethanol in 1.3 l of boiling xylene and allowed to react for a further 0.5 hours. Approximately 700 of azeotrope is distilled off. The reaction mixture is hydrolysed at 80° to 100° C. by rapid addition to a mixture of 300 ml of concentrated (37%) hydrochloric acid and 500 g of crushed ice. The organic layer separated off is washed twice, each time with 150 ml of semi-concentrated hydrochloric acid. The combined aqueous extracts are heated for 2 hours under vigorous reflux and then evaporated to dryness in vacuo. The residue is extracted hot from 600 ml of isopropanol and crystallised. The residue filtered off is dried to constant weight in vacuo at elevated temperature. A second crop of material can be obtained by concentrating the mother liquor to a volume of approximately 100 ml. 44.3 g (27.1%) of 1-methyl-perhydroazepin-4-one HCl is obtained.

Melting point: 159°–161° C. (decomposition)

Example 10

181.8 g of n-butyl 4-(2-carbethoxyethyl(2-phenyl-ethyl) amino)butyrate (content: 93%) is charged evenly, under nitrogen, over a period of 2 to 3 hours at the top of a packed column into a solution of 61.7 g of potassium tert-butylate in 1.5 l of boiling xylene and the mixture is allowed to react for a further 1 to 1.5 hours. Approximately 500 ml of distillate is withdrawn. The reaction mixture is hydrolysed at 50° to 80° C. by rapid addition to a mixture of 200 ml of concentrated (37%) hydrochloric acid and 300 g of crushed ice. The organic layer separated off is washed twice, each time with 100 ml of semi-concentrated hydrochloric acid. The combined aqueous extracts are heated for 2 hours under vigorous reflux and then evaporated to dryness in vacuo. The residue is suspended hot in 250 ml of isopropanol and crystallised in the cold. The crystallisate is exhaustively extracted from isopropanol and crystallised. The residue filtered off is dried to constant weight in vacuo at elevated temperature. 95.4 g (80.8%) of 1-(2-phenylethyl)-perhydroazepin-4-one HCl is obtained.

Melting point: 196°–197° C. (decomposition)

Example 11

153.7 g of methyl 4-(2-carbomethoxyethyl(2-phenyl-ethyl)amino)butyrate (content: 96%) is charged evenly, under nitrogen, over a period of 2 to 3 hours at the top of a packed column into a solution of 61.7 g of potassium tert-butylate in 1.5 l of boiling xylene. During the reaction a sticky precipitate forms which dissolves completely at the end of the reaction. The mixture is allowed to react for a further 1 to 1.5 hours. Approximately 500 l of azeotrope is distilled off. The reaction mixture is hydrolysed at 50° to 80° C. by rapid addition to a mixture of 200 ml of concentrated (37%) hydrochloric acid and 300 g of crushed ice. The organic layer separated off is washed twice, each time with 100 ml of semi-concentrated hydrochloric acid. The combined aqueous extracts are heated for 2 hours under vigorous reflux and then evaporated to dryness in vacuo. The residue is exhaustively extracted from isopropanol and crystallised. The residue filtered off is dried to constant weight in a vacuum at elevated temperature. A second crop of material can be obtained by concentrating the mother liquor to a volume of approximately 100 ml. 105.4 g (86.5%) of 1-(2-phenylethyl)perhydroazepin-4-one HCl is obtained.

Melting point: 196°–198° C. (decomposition)

Example 12

245.3 g of ethyl 4-(2-carbethoxyethylmethylamino) butyrate is added over a period of 3 minutes, under nitrogen, to a solution of 123.4 g of potassium tert-butylate in 1.3 l of boiling xylene, with 300 ml of solvent being rapidly distilled off, and the mixture is allowed to react for a further 0.5 hours. A further 350 ml of azeotrope is distilled off. The reaction mixture is hydrolysed at 80° to 100° C. by rapid addition to a mixture of 300 ml of concentrated (37%) hydrochloric acid and 500 g of crushed ice. The organic layer separated off is washed twice, each time with 150 ml of semi-concentrated hydrochloric acid. The combined aqueous extracts are heated for 2 hours under vigorous reflux and then evaporated to dryness in vacuo. The residue is extracted hot from 600 ml of propanol and crystallised. The residue filtered off is dried to constant weight in vacuo at elevated temperature. A second crop of material can be obtained by concentrating the mother liquor to a volume of approximately 100 ml. 78.3 g (47.9%) of 1-methylhydroazepin-4-one HCl is obtained.

Melting point: 164°–165° C. (decomposition)

We claim:

1. Improved method for the preparation of hexahydroazepinones and hexahydroazepinoles of the general formula I:

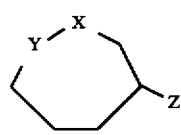

and the salts thereof,
wherein
X signifies —$CH_2$—
Y signifies —N(—R)—, —N(—$CH_3$)—, N(—$CH_2$—$CH_2$—$C_6H_5$)— and
Z signifies =O, —OH
wherein in each case R represents H, alkyl, cycloalkyl, aralkyl, aryl, by means of the Dieckmann condensation using strong bases in inert solvents, characterized by the following steps:
a) using an excess of up to a maximum of 20% of strong bases,
b) carrying out the condensation reaction over reaction times of from 1 to 6 hours,
c) conducting the operation with concentrations of from 0.1 to 1.5 mol of the undiluted 1,8-dicarboxylic acid ester flowing in to be condensed, of the formula II

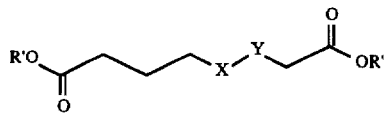

wherein X is —$CH_2$—
wherein Y signifies —N(—R)—, —N(—$CH_3$)—, —N(—$CH_2$—$CH_2$—$C_6H_5$)—
wherein R' signifies an alkyl, isoalkyl, cycloalkyl, aralkyl, aryl group, per liter of solvent,
d) carrying out the reaction in a loop-reactor, circulating the dissolved base and charging the undiluted dicarboxylic acid ester into the circulation system by means of a jet nozzle, thereby, avoiding a conventional dilution technique, or simultaneously diluting and heating in a packed column undiluted 1,8-dicarboxylic ester introduced at the top of the column with the ascending condensate formed.

2. Preparation and isolation of hexahydroazepinoles and the salts thereof through reduction of the hexahydroazepinones according to claim 1 by means of complex hydrides or by catalytic hydrogenation in water or alcohols.

3. The method of claim 1, wherein the condensation reaction step is carried out for 1 to 3 hours.

4. The method of claim 1, wherein the concentration of undiluted 1,8-dicarboxylic acid ester is 0.3 to 0.9 mol per liter of solvent.

5. The method of claim 1, wherein the solvent is xylene.

6. The method of claim 1, further comprising the step of synthesizing pharmaceutically active azelastine from the hexahydroazepinones and hexahydroazepinoles produced.

7. The method of claim 1, further comprising the step of synthesizing pharmaceutically active flezelastine from the hexahydroazepinones and hexahydroazepinoles produced.

8. An improved method for the preparation of hexahydroazepinones and hexahydroazepinoles of the general formula I:

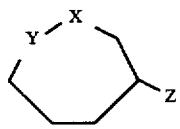

and the salts thereof,
wherein X signifies —$CH_2$—
Y signifies —N(—$CH_3$)—, —N(—$CH_2$—$CH_2$—$C_6H_5$)— and Z signifies =O, —OH
wherein in each case R represents H, alkyl, cycloalkyl, aralkyl, aryl, by means of the Dieckmann condensation using strong bases in inert solvents, characterized by the following steps:
a) reacting a 1,8-dicarboxylic acid ester of the formula II:

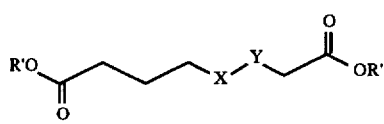

wherein X is —$CH_2$—
wherein Y signifies —N(—R)—, —N(—$CH_3$)—, —N(—$CH_2$—$CH_2$—$C_6$—$H_5$)—
wherein R' signifies an alkyl, isoalkyl, cycloalkyl, aralkyl, aryl group,
with the strong bases in the inert solvent, wherein the 1,8-dicarboxylic acid ester is in a concentration of from 0.1 to 1.5 mol per liter of solvent, and the base is in an excess of up to a maximum of 20%,
c) carrying out the reaction in a loop-reactor for 1 to 6 hours, wherein the dissolved base is circulated and the undiluted 1,8-dicarboxylic acid ester is charged into the circulation system by means of a jet nozzle, or simultaneously diluting and heating in a packed column the undiluted 1,8-dicarboxylic acid ester introduced at the top of the column with the ascending condensate formed.

* * * * *